(12) United States Patent
Thomas et al.

(10) Patent No.: US 7,297,100 B2
(45) Date of Patent: Nov. 20, 2007

(54) DEVICE FOR MAGNETIC AND ELECTRIC FIELD SHIELDING

(75) Inventors: Alex W. Thomas, London (CA); Frank S. Prato, London (CA); Elena Choleris, London (CA)

(73) Assignee: Fralex Therapeutics, Inc., Toronto, Ontario (CA)

( * ) Notice: Subject to any disclaimer, the term of this patent is extended or adjusted under 35 U.S.C. 154(b) by 533 days.

(21) Appl. No.: 10/313,616

(22) Filed: Dec. 6, 2002

(65) Prior Publication Data

US 2003/0217754 A1 Nov. 27, 2003

Related U.S. Application Data

(63) Continuation of application No. PCT/CA01/00829, filed on Jun. 7, 2001.

(60) Provisional application No. 60/210,478, filed on Jun. 9, 2000.

(51) Int. Cl.
*A61N 1/00* (2006.01)
(52) U.S. Cl. ...................................................... 600/14
(58) Field of Classification Search .............. 600/9–15; 128/898
See application file for complete search history.

(56) References Cited

U.S. PATENT DOCUMENTS

| | | | |
|---|---|---|---|
| 3,394,260 A * | 7/1968 | Phipps ..................... | 250/516.1 |
| 3,678,337 A | 7/1972 | Grauvogel et al. | |
| 4,030,892 A * | 6/1977 | Mendelsohn et al. ....... | 442/186 |
| 4,097,631 A * | 6/1978 | Wilken ....................... | 428/114 |
| 4,583,545 A | 4/1986 | Towe | |
| 4,825,877 A | 5/1989 | Kempe | |
| 5,000,178 A * | 3/1991 | Griffith ..................... | 607/2 |
| 5,014,699 A * | 5/1991 | Pollack et al. ............ | 607/2 |
| 5,045,637 A * | 9/1991 | Sato et al. ............. | 174/35 MS |
| 5,066,272 A | 11/1991 | Eaton et al. | |
| 5,084,003 A | 1/1992 | Susic | |
| 5,260,128 A * | 11/1993 | Ishii et al. ................. | 428/328 |
| 5,342,410 A | 8/1994 | Braverman | |
| 5,527,259 A | 6/1996 | Grace et al. | |
| 5,578,359 A * | 11/1996 | Forbes et al. .............. | 428/131 |
| 5,621,188 A * | 4/1997 | Lee et al. ............. | 174/35 MS |
| 5,634,939 A | 6/1997 | Kuster et al. | |
| 5,690,109 A | 11/1997 | Govind et al. | |
| 5,725,471 A | 3/1998 | Davey | |

(Continued)

FOREIGN PATENT DOCUMENTS

DE 33 31 976 3/1985

(Continued)

OTHER PUBLICATIONS

Baker, Timothy B., "Morphine Tolerance as Habituation", *Psychological Review*, vol. 92, No. 1, (1985),78-108.

(Continued)

*Primary Examiner*—Samuel G Gilbert
(74) *Attorney, Agent, or Firm*—John S. Child, Jr.

(57) ABSTRACT

The invention is directed to the use of magnetic shielding alone and magnetic shielding combined with magnetic field stimulation in methods for the treatment, diagnosis and assessment of disease, condition, or physical or mental state. The invention also includes portable devices for the shielding of magnetic fields for therapy and treatment of disease, condition, or physical or mental state.

12 Claims, 4 Drawing Sheets

U.S. PATENT DOCUMENTS

| | | | |
|---|---|---|---|
| 5,807,272 | A | 9/1998 | Kun et al. |
| 5,833,600 | A | 11/1998 | Young |
| 5,935,054 | A | 8/1999 | Loos |
| 5,968,854 | A * | 10/1999 | Akopian et al. ............ 442/132 |
| 6,128,522 | A | 10/2000 | Acker |
| 6,179,772 | B1 * | 1/2001 | Blackwell .................... 600/13 |
| 6,198,958 | B1 | 3/2001 | Ives et al. |
| 6,234,953 | B1 | 5/2001 | Thomas et al. |
| 6,312,376 | B1 | 11/2001 | Koren et al. |
| 6,520,903 | B1 | 2/2003 | Yamashiro |
| 6,547,713 | B1 | 4/2003 | Talpo |
| 6,687,525 | B2 | 2/2004 | Llinas et al. |
| 2002/0169355 | A1 | 11/2002 | Rohan |
| 2003/0023159 | A1 | 1/2003 | Philipp |
| 2003/0181791 | A1 | 9/2003 | Thomas |
| 2003/0217754 | A1 | 11/2003 | Thomas |
| 2006/0106274 | A1 | 5/2006 | Thomas |

FOREIGN PATENT DOCUMENTS

| | | |
|---|---|---|
| DE | 39 38 920 | 5/1991 |
| EP | 1138348 | 10/2001 |
| FR | 2 533 131 | 3/1984 |
| GB | 2025237 | 1/1980 |
| GB | 2143131 | 2/1985 |
| GB | 2270000 | 2/1994 |
| WO | WO-97/46277 | 12/1997 |
| WO | WO-98/47565 | 10/1998 |
| WO | WO 00/07684 | 2/2000 |
| WO | WO 00/76582 | 12/2000 |

OTHER PUBLICATIONS

Baker-Price, L. A., "Weak, But Complex Pulsed Magnetic Fields May Reduce Depression Following Traumatic Brain Injury", *Preceptual and Motor Skills*, 83, (1996),491-498.

Barker, A. T., "Magnetic Stimulation of the Human Brain and Peripheral Nervous Systems: An Introduction and the Results of an Initial Clinical Evaluation", *Neurosurgery*, 20(1), (1987), 100-109.

Betancur, Catalina, "Magnetic field effects on stress-induced analgesia in mice: modulation by light", *Neuroscience Letters 182*, (1994), 147-150.

Choleris, E., "A Detailed Ethological Analysis of the Mouse Open Field Test: Effects of Diazepam, Chlordiazepoxide and an Extremely Low Frequency Pulsed Magnetic Field", *Neuroscience and Biobehavioral Reviews*, 25, (2001), 235-260.

Choleris, E., "Shielding but not zeroing of the ambient magnetic field reduces stress-induced analgesia in mice", *The Royal Society*, (2001).

Del Seppia, Cristina, "Exposure to a Hypogeomagnetic field Or To Oscillating Magnetic Fields Similarly Reduce Stress-Induced Analgesia in C57 Male Mice", *Life Sciences*, vol. 66, No. 14, (2000), 1299-1306.

Del Seppia, Cristina, "Exposure to Oscillating Magnetic Fields Influences Sensitivity to Electrical Stimuli, I. Experiments on Pigeons", *Bioelectromagnetics 16*, (1995), 290-294.

Deutshlander, Mark E., "The Case for Light-Dependent Magnetic Orientation In Animals", *The Journal of Experimental Biology 202*, (1999), 891-908.

Dyakonova, V. E., "Complex Avoidance Behaviour and its Neurochemical Regulation in the Land Snail *Cepaea nemoralis*", *Gen. Pharmac.*, vol. 26, No. 4 (1995), 773-777.

Grisel, Judith E., et al., "Associative and non-associative mechanisms of morphine analgesic tolerance are neurochemically distinct in the rat spinal cord", *Psychopharmacology 128*, (1996), 248-255.

Kavaliers, Martin, "A Functional Role for an Opiate System in Snail Thermal Behavior", *Science*, vol. 220, (1983), 99-101.

Kavaliers, Martin, "Brief exposure to 60Hz magnetic fields improves sexually dimorphic spatial learning performance in the meadow vole, *Microtus pennsylvanicus*", *Journal of Comparative Physiology A*, 173, (1993), 241-248.

Kavaliers, Martin, "Opioid Systems and Magnetic Field Effects in the Land Snail, *Cepaea nemoralis*", *Biol Bull. 180*, (Apr. 1991), 301-309.

Kavaliers, Martin, "Opioid Systems and the Biological Effects of Magnetic Fields", *On the Nature of Electromagnetic Field Interactions with Biological Systems*, Chapter 13, (1994),181-193.

Kavaliers, Martin, "Repeated naloxone treatments and exposures to weak 60-Hz magnetic fields have 'analgesic' effects in snails", *Brain Research*, 620, (1993), 159-162.

Kavaliers, Martin, "Spatial learning in deer mice: sex differences and the effects of endogenous opioids and 60 Hz magnetic fields", *J Comp Physiol A*, 179, (1996), 715-724.

Kavaliers, Martin, et al., "Tolerance to Morphine-Induced Analgesia in Mice: Magnetic Fields Function As Environmental Specific Cues and Reduce Tolerance Development", *Life Science*, vol. 37, (1985), 1125-1135.

Kavaliers, M., "Tolerance to the Morphine-Influenced Thermal Response in the Terrectrial Snail, *Cepea nemoralis*", *Neuropharmacology*, vol. 22, No. 11, (1983), 1321-1326.

Kits, Karel S., "Voltage gated calcium channels in molluscs: classification, $Ca^{2+}$ dependent inactivation, modulation and functional roles", *Invetebrate Neuroscience*, 2, (1996), 9-34.

Lednev, V. V., "Magnetic Parametric Resonance in Biosystems: Experimental Verificaiton of the Predictions of a theory using regenerating planarians *Dugesia tigrina* as a Test System", *Biophysics*, vol. 41, No. 4, (1996), 825-835.

McLeod, Kenneth J., "Frequency Dependence of Electric Field Modulation of Fibroblast Protein Synthesis", *Science, New Series*, vol. 236, No. 4807, (1987), 1465-1469.

Michon, Andre , "Attempts to Simulate the Association Between Geomagnetic Activity and Spontaneous Seizures in Rats Using Experimentally Generated Magnetic Fields", *Perceptual and Motor Skills*, 82, (1996),619-626.

Papi, Floriano, "Exposure to Oscillating Magnetic Fields Influences Sensitivity to Electrical Stimuli, II. Experiments on Humans", *Bioeletromagnetics 16*, (1995), 295-300.

Papi, Floriano, "Orientation-Disturbing Magnetic Treatment Affects The Pigeon Opioid System", *J. exp. Biol.*, 166, (1992), 169-179.

Polk, Charles, "Dosimetry of Extremely-Low-Frequency Magnetic Fields", *Bioeletromagnetics Supplement 1*, (1992), 209-235.

Prato, Frank S., "Attenuation of Morphine-Induced Analgesia in Mice By Exposure to Magnetic Resonance Imaging: Separate Effects Of The Static, Radiofrequency and Time-Varying Magnetic Fields", *Magnetic Resonance Imaging*, vol. 5, (1987), 9-14.

Prato, Frank S., "Behavioural Evidence That Magnetic Filed Effects in the Land Snail, *Cepaea nemoralis*, Might Not Depend on Magnetite or Induced Electric Currents", *Bioelectromagnetics 17*, (1996),123-130.

Prato, F. S., "Extremely Low Frequency Magnetic Fields Can Either Increase or Decrease Analgaesia in the Land Snail Depending on Field and Light Conditions", *Bioelectromagnetics*, 21, (2000), 287-301.

Prato, F. S., "Human Standing Balance is Affected by Exposure to Pulsed ELF Magnetic Fields: Light Intensity-Dependent Effects", *Neurophysiology, Basic and Clinical NeuroReport*, 12(7), (2001), 1-5.

Prato, Frank S., "Possible mechanisms by which extremely low frequency magnetic fields affect opioid function", *The FASEB Journal*, vol. 9, (Jun. 1995), 807-814.

Rothman, Richard B., "A Review of the Role of Anti-Opioid Peptides in Morphine Tolerance and Dependence", *Synapse 12*, (1992), 129-138.

Thomas, A. W., "A Comparison of Rheumatoid Arthritis and Fibromyalgia Patients and Healthy Controls Exposed to a Pulsed (200 u T) Magnetic Field: Effects on Normal Standing Balance", *Neuroscience Letters*, 309, (2001), 17-20.

Thomas, Alex W., "Analgesic Effects of a Specific Pulsed Magnetic Field in the Land Snail, *Cepaea nenoralis*: Consequences of Repeated Exposures, Relations to Tolerance and Cross-Tolerance with DPDPE", *Peptides*, vol. 19, No. 2, (1998), 333-342.

Thomas, Alex W., "Antinociceptive effects of a pulsed magnetic field in the land snail, *Cepaea nemoralis*", *Neuroscience Letters 222*, (1997), 107-110.

Thomas, Alex W., "Daily Post-training Exposure to Pulsed Magnetic Fields That Evoke Morphine-Like Analgesia Affects Consequent Motivation but not Proficiency in Maze Learning in Rats", *Electro- And Magnetobiology*, 16(1), (1997), 33-41.

Thomas, A. W., "Human Subjects Exposed to a Specific Pulsed (200 u T) Magnetic Field: Effects on Normal Standing Balance", *Neuroscience Letters*, 297, (2001), 121-124.

Thomas, A. W., "Magnetic Field Exposure and Behavioral Monitoring System", *Bioelectromagnetics*, 22, (2001), 401-407.

Thomas, Alex W., "Pulsed Magnetic Field Induced "Analgesia" in the Land Snail, *Cepaea nemoralis*, and the Effects of μ, δ, and κ Opioid Receptor Agonists/Antagonists", *Peptides*, vol. 18, No. 5, (1997), 703-709.

Tian, Jin-Hua, "Involvement of endogenous Orphanin FQ in electroacupuncture-induced analgesia", *NeuroReport 8*, (1997), 497-500.

Tiffany, Stephen T., "Morphine Tolerance in Rats: Congruence With a Pavlovian Paradigm", *Journal of Comparative and Physiological Psychology*, vol. 95, No. 5, (1981), 747-762.

Tiffany, Stephen, "Tolerance to Morphine in the Rat: Associative and Nonassociative Effects", *Behavioral Neuroscience*, vol. 102, No. 4, (1988), 534-543.

Weaver, James C., "The Response of Living Cells to Very Weak Electric Fields: The Thermal Noise Limit", *Reports*, (1990) ,459-462.

Kirschvink, "Particle-size . . . ," Contribution No. 4135 from the division of Geological and Planetary Sciences, California Institute of Technology, pp. 243-256, (1985).

Papi, et al., "Exposure to oscillating magnetic fields . . . ," Bioelectromagnetics, 16:295-300, (1995).

Del Seppia, et al., "Exposure to oscillating magnetic fields influences sensitivity to electrical stimuli I. Experiments on pigeons," Bioelectromagnetics, 16:290-294, (1995).

Bassett, et al., "Treatment of ununited tibial diaphyseal fractures with pulsing electromagnetic fields," J. Bone Joint Surg. 63-A4:511-523, (1981).

Beckers, G and Homberg, V (1991): Impairment of visual perception and visual short term memory scanning by transcranial magnetic stimulation of occipital cortex. Exp Brain Res 87:421-432.

Bell, GB, Marino, AA and Chesson, AL (1992): Alerations in brain electrical activity caused by magnetic fields: Detecting the detection process. Electroenceph Clin Neurophysiol 83:389-397.

Bell, GB, Marino, AA and Chesson, AL (1994): Frequency-specific blocking in the human brain caused by electromagnetic fields. NeuroReport 5:510-512.

Bell, GB, Marino, A, Chesson, A and Struve, F (1992): Electrical states in the rabbit brain can be altered by light and electromagnetic fields. Brain Res 570:307-315.

Canady, DJ and Lee, RC (1991): Scientific basis for clinical applications of electrical fields in soft tissue repair, in Electromagnetics in Medicine and Biology, Brighton, C T and Pollack, SR (eds.). San Francisco Press, 275-280.

Carson, JJL, Prato, FS, Drost, DJ, Diesbourg, LD and Dixon, SJ (1990): Time-varying magnetic fields increase cytosolic free $Ca^2$ in H-60 cells. Am J Physiol Soc 259 (Cell Physiol 28): C687-C692.

Fleischmann, A, Prolov, K, Abarbanel, J and Belmaker, RH (1995): The effect of transcranial magnetic stimulation of rat brain on behavioral models of depression. Brain Res 699:130-132.

Frey, A.H. (ed.) (1994): On the Nature of Electromagnetic Field Interactions with Biological Systems, R.G. Landes Co., Austin, Texas.

Fuller, M, Dobson, J, Wieser, HG and Moser, S (1995): On the sensitivity of the human brain to magnetic fields: Evocation of epileptiform activity. Brain Res Bull 36:155-169.

Grisaru, N, Yaroslavsky, U, Abarbanel, J, Lambert, T and Belmaker, RH (1994): Transcranial. magnetic stimulation in depression and schizophrenia. Eur Neuropsychopharmacol 4:287-288.

Holden, C (1995): Substitute for shock therapy? Science 1/DEC, 270, 5241-1443.

Ito, H and Bassett, Cal (1983): Effect of weak, pulsing electromagnetic fields on neural regeneration in the rat. Clin Orthopaed 181:283-290.

Kavaliers, M and Ossenkopp, K-P (1985): Exposure to rotating magnetic fields alters morphine-induced behavioral responses in two strains of mice. Neuropharmacol 24:4:337-340.

Kavaliers, M and Ossenkopp, K-P (1986): Magnetic fields differentially inhibit mu, delta, kappa and sigma opiate-induced analgesia in mice. Peptides 7: 449-453.

Kavaliers, M and Ossenkopp, K-P (1986b): Stress-induced opioid analgaesia and activity in mice: Inhibitory influences of exposure to magnetic fields. Psychopharmacol 89:440-443.

Kavaliers, M and Ossenkopp, K-P (1986): Magnetic field inhibition of morphine-induced analgesia and behavioral activity in mice: Evidence for involvement of calcium ions. Brain Res 379:30-38.

Kavaliers, M and Ossenkopp, K-P (1987): Calcium channel involvement in magnetic field inhibition of morphine-induced analgesia. Naunyn-Schmiedeberg's Arch Pharmacol 336:308-315.

Kavaliers, M and Ossenkopp, K-P (1988): Magnetic fields inhibit opioid-mediated "analgesic" behaviours of the terrestrial snail, *Cepaea nemoralis*. J Comp Physiol A 162:551-558.

Kavaliers, M, Ossenkopp, K-P and Hirst, M (1984): Magnetic fields abolish the enhanced nocturnal analgesic response to morphine in mice. Physiol Behav 32:261-264.

Kavaliers, M, Ossenkopp, K-P and Tysdale, DM (1991): Evidence for the involvement of protein kinase C in the modulation of morphine-induced "analgesia" and the inhibitory effects of exposure to 60-Hz magnetic fields in the snail, *Cepaea nemoralis*. Brain Res 554: 65-71.

Kwong-Hing, A, Sandhu, HS, Prato, FS, Frappier, JRH and Kavaliers, M (1989): Effects of magnetic resonance imaging (MRI) on the formulation of mouse dentin and bone. J Exper Zool 252:53-59.

Lerchl, A, Honaka, KO and Reiter, RJ (1991): Pineal gland "magnetosensitivity" to static magnetic fields is a consequence of induced electric currents (eddy currents). J Pineal Res 10:109-116.

Lindstrom, E, Lindstrom, P, Berglund, A, Mild, KH and Lundgren, E (1993): Intracellular calcium oscillations induced in a T-cell line by a weak 50 Hz magnetic field. J Cell Physiol 156:395-398.

Lohmann, KJ and Willows, AOD (1991): An identifiable molluscan neuron responds to changes in earth-strength magnetic fields. J exp Biol 161:1-24.

Lyskov, E, Juutilainen, J, Jousmaki, V, Hänninen, O, Medvedev, S and Partamem, J (1993): Influence of short-term exposure of magnetic field on the bioelectrical processes of the brain and performance. Intern J Psychophysiol 14:227-231.

Mather, JG and Baker, RR (1981): Magnetic sense of direction in woodmice for route-based navigation. Nature 291:152-155.

Ossenkopp, K-P and Kavaliers, M (1987): Morphine-Induced analgesia and exposure to low-intensity 60-Hz magnetic fields: inhibition of nocturnal analgesia in mice is a function of magnetic field intensity. Brain Res 418:356-360.

Ossenkopp, K-P and Cain, DP (1988): Inhibitory effects of acute exposure to low-intensity 60-Hz magnetic fields on electrically kindled seizures in rats. Brain Res 442:255-260.

Winston, C, Parris, V, Janicki, PK, Johnson, BW, JR., and Matthews, L (1994): The behavioral and biochemical effect of pulsating magnetic field treatment (PMFT) on chronic pain produced by chronic constriction injury of sciatic nerve in rat. Analgesia 1:1:57-64.

Pascual-Leone, A, Valls-Solé, J, Brasil-NETOo, JP Cammarota, A, Grafman, J and Hallett, M (1994): Akinesia in Parkinson's Disease. II. Effects of subthreshold repetitive transcranial motor cortex stimulation. Neurology 44:892-898.

Phillips, JB and Borland, SC (1992): Behavioural evidence for the use of a light-dependent magnetoreception mechanisms by a vertebrate. Nature 359:142-144.

Phillips, JB and Sayeed, O (1983): Wavelength-dependent effects of light on magnetic compass orientation in *Drosophila melanogaster*. J Comp Physiol A 172: 303-308.

Prato, FS, Frappier, JRH, Shivers, RR, Kavaliers, M, Zabel, P, Drost, D and Lee, T-Y (1990): Magnetic resonance imaging increases the blood-brain barrier permeability to 153-gadolinium diethylenetriaminepentaacetic acid in rats. Brain Res 523:301-304.

Prato, FS, Wills, JM, Frappier, JRH, Drost, DJ, Lee, T-Y, Shivers, RR and Zabel, P (1994): Blood-brain barrier permeability in rats is altered by exposure to magnetic fields associated with magnetic resonance imaging at 1.5T. Microscopy Research and Technique 27:528-534.

Reiter, RJ (1992): Alterations of the circadian melatonin rhythm by the electromagnetic spectrum: A study in environmental toxicology. Reg Toxicol Pharmacol 15:226-244.

Reiter, RJ and Richardson, BA (1992): Magnetic field effects on pineal indoleamine metabolism and possible biological consequences. FASEB J 6:2283-2287.

Schneider, T, Thalau, H-P and Semm, P (1994): Effects of light or different earth-strength magnetic fields on the nocturnal melatonin concentration in a migratory bird. Neurosci Lett 168:73-75.

Selmaoui, B and Touitou, Y (1995): Sinusoidal 50Hz magnetic fields depress rat pineal NAT activity and serum melatonin: Role of duration and Intensity of exposure. Life Sci 57:1351-1358.

Semm, P and Beason, RC (1990): Response to small magnetic variations by the trigeminal system of the bobolink. Brain Res Bull 25:735-740.

Semm, P, Schneider, T and Vollrath, L (1980): Effects of an earth-strength magnetic field on electrical activity of pineal cells. Nature 288:607-608.

Shivers, RR, Kavaliers, M, Teskey, GC, Prato, FS and Pelletier, R-M (1987): Magnetic resonance imaging temporarily alters blood-brain barrier permeability in the rat. Neurosci Lett 76:25-31.

Sisken, BF, Kanje, J, Lundborg, G and Kurtz, W (1990): Pulsed electromagnetic fields stimulate nerve regeneration in vitro and in vivo. Restor Neurol Neurosci 1:303-309.

Steffensen, B, Caffesse, RG, Hanks, CT, Avery, JK and Wright, N (1988): Clinical effects of electromagnetic stimulation as an adjunct to periodontal therapy. J Periodontol JAN/88 59:1:46-52.

Teskey, GC, Prato, FS, Ossenkopp, K-P and Kavaliers, M (1988): Exposure to time varying magnetic fields associated with magnetic resonance imaging reduces fentanyl-induced analgesia in mice. Bioelectromagnetics 9:2:167-174.

Thomas, AW, Kavaliers, M and Prato, FS (1996): Antinociception ("analgesia") induced by weak extremely low frequency complex neuroelectro-magnetic pulses. Bioelectromagnetics Soc Abstracts 18, in press.

Thomas, AW, Kavaliers, M and Prato, FS (1996): Development of tolerance to the opioid-mediated antinociceptive effects of weak extremely low frequency complex neuroelectromagnetic pulses. Bioelectromagnetics Soc Abstracts 18, in press.

Walleczek, J (1992): Electromagnetic field effects on cells on the immune system: The role of calcium signalling, FASEB J 6:3177-3185.

Walleczek, J and Liburdy, RP (1990): Nonthermal 60 Hz sinusoidal magnetic-field exposure enhances $^{45}Ca^{2+}$ uptake in rat thymocytes: dependence on mitogen activation. FEBS 271:1,2:157-160.

Zyss, T (1994): Deep magnetic brain stimulation—The end of psychiatric electroshock therapy? Medical Hypotheses 43: 69-74.

Kavaliers, M and Ossenkopp, K-P (1993): Repeated naloxone treatments and exposures to weak 60-Hz magnetic fields have "analgesic" effects in snails. Brain Res 620: 159-162.

Persinger, MA, Koren, SA, Makarec, K, Richards, P and Youlton, S (1991): Differential effects of wave form and the subject's possible temporal lobe signs upon experiences during cerebral exposure to weak intensity magnetic fields. J Bioelectricity 10(1&2):141-184.

Richards, PM, Persinger, MA and Koren, SA (1993): Modification of activation and evaluation properties of narratives by weak complex magnetic field patterns that simulate limbic burst firing. Intern J Neurosci 71:71-85.

Gillis, C and Persinger, MA (1993): Shifts in the Plutchik emotion profile indices following three weekly treatments with pulsed vs continuous cerebral magnetic fields. Perceptual and Motor Skills 76:168-170.

Tiller, SG and Persinger, MA (1994): Enhanced hypnotizability by cerebrally applied magnetic fields dependes upon the order of hemispheric presentation: An anisotropic effect. Intern J Neurosci 79:157-163.

Persinger, MA, Richards, PM and Koren, SA (1994): Differential ratings of pleasantness following right and left hemispheric application of low energy magnetic fields that stimulate long-term potentiation. Intern J Neurosci 79:191-197.

Bureau, YRJ and Persinger, MA (1995): Decreased incidence of limbic motor seizures following twenty pairings of subclinical lithium-pilocarpine injections and a complex "burst-firing" magnetic field. Electro- and Magnetobiology 14(1):1-6.

Persinger, MA, Ludwig, HW and Ossenkopp, K-P (1973): Psychophysiological effects of extremely low frequency electromagnetic fields: a review. Perceptual and Motor Skills, Monograph Supplement 3-V36. 36:1131-1159.

Persinger, MA (1988): The Modern Magnetotherapies, in Marion AA (ed.) Modern Bioelectricity, NY, Dekker:589-627.

Persinger, MA (1995): On the possibility of directly accessing every human brain by electromagnetic induction of fundamental algorithms. Perceptual and Motor Skills 80:791-799.

Adey, WR (1973): The influences of impressed electrical fields at EEG frequencies on brain and behavior. Behavior and Brain Electrical Activity, BURCH, [ ] and Alshuler, [ ], eds., NY, Plenum: 363-390.

Fleming, JL, Persinger, MA and Koren, SA (1994): Magnetic pulses elevate nociceptive thresholds: comparisons with opiate receptor compounds in normal and seizure-induced brain-damaged rats. Electro- and magnetobiololgy 13(1):67-75.

Choleris, E., et al., "A detailed ethological analysis of the mouse open field test: effects of diazepam, chlordiazepoxide and an extremely low frequency pulsed magnetic field," Neuroscience and Biobehavioral Reviews, 25:235-260, (2001).

Prato, F.S., et al., "Extremely low frequency magnetic fields can either increase or decrease analgaesia in the land snail depending on field and light conditons," Bioelectromagnetics, 21:287-301, (2000).

Prato, F.S., et al., "Human standing balance is affected by exposure to pulsed ELF magnetic fields: light intensity-dependent effects," NeuroReport, 12:1-5, (2001).

Thomas, A.W., et al., "A comparison of rheumatoid arthritis and fibromyalgia patients and healthy normal controls exposed to a pulsed (200 µT) magnetic field: effects on normal standing balance," Neuroscience Letters, 309:17-20, (2001).

Thomas, A.W., et al., "Human subjects exposed to a pulsed (200 µT) magnetic field: effects on normal standing balance," Neuroscience letters, 297:121-124, (2001).

Thomas, A.W., et al., "Magnetic field exposure and behavioral monitoring system," Bioelectromagnetics, 22:401-407, (2001).

Del Seppia C., et al., "Exposure to a hypogeomagnetic field or to oscillating magnetic fields similarly reduce stress-induced annualise in C57 mice," Life Sciences 66:1299-1306 (2000).

Deutschlander, ME., et al., "The case of light-dependent magnetic orientation in animals," J. Exp. Biol., 202:891-908, (1999).

Choleris, E., "Shielding but not zeroing of the ambient magnetic field reduces stress-induced analgesia in mice," The Royal Society, (2001).

* cited by examiner

DEVICE FOR MAGNETIC AND ELECTRIC FIELD SHIELDING

RELATED APPLICATIONS

This application is a continuation under 35 U.S.C. 111(a) of PCT/CA01/00829 filed Jun. 7, 2001 and published in English as WO 01/93949 A1 on Dec. 13, 2001, which claims priority from U.S. Provisional Patent Application Ser. No.: 60/210,478 filed Jun. 9, 2000, which application and publication are incorporated herein by reference.

FIELD OF INVENTION

The invention relates to the use of magnetic shielding and magnetic field stimulation in a method for the treatment, diagnosis and assessment of disease. The invention also provides a device for the shielding of magnetic fields for therapy and treatment of disease.

BACKGROUND OF THE INVENTION

It has been demonstrated that an animals' behaviour can be altered by exposure to extremely low frequency (ELF) magnetic fields. This includes navigation, migration and homing in birds, insects and newts (Deutschlander et al, 1998) and alteration of opioid-induced analgesia in molluscs, birds and rodents (Betancur et al, 1994). There is also evidence that extremely low frequency magnetic fields have effects on behaviour in humans (Thomas et al, 1998; Papi et al, 1995). Increasing evidence suggests that pulsed ELF fields, also called Cnps, can be used for both therapeutic (Thomas et al, 1998) and diagnostic (Thomas et al, 2000) purposes. However, the magnetic field intensities required for diagnostic and treatment uses are approximately 40 to 200 $\mu$T, a magnetic field intensity similar to the Earth's magnetic field. The electric power required to generate fields of such intensity is very large and requires a fixed and relatively expensive apparatus.

Recent experiments have demonstrated that under ELF magnetic field shielding, rodents could sense the absence of weak (<0.1 $\mu$T) ELF fields (Del Seppia et al, 2000). Stress-induced analgesia appeared to be attenuated or abolished in mice placed in a magnetic field shielded box where there is an absence of ambient ELF fields when the wide-spectrum geomagnetic field is effectively zeroed. Under geomagnetic shielded conditions, animals appeared sensitive to weak ELF magnetic fields. Under shielded conditions, the behaviour of mice was modified by the absence of an ELF magnetic field of 0.1 $\mu$T intensity compared to a nominal 10-100 $\mu$T MF needed to modify behaviour (Choleris et al, 2001).

It has also been demonstrated (Kavaliers and Ossenkopp, 1993) that exposure to ELF magnetic fields (circa 100 $\mu$T) can attenuate opioid-induced analgaesia. Paradoxically, it has been suggested that daily repeated exposures to such ELF fields may induce analgesia (Kavaliers and Ossenkopp, 1985, 1993).

The Applicant has now developed a method involving daily repeated exposures to reduced ambient fields to induce analgesia in humans for clinical use. The Applicant has demonstrated that analgesia may be effectively achieved in humans by daily repeated exposures in a magnetically shielded room. Analgesia of individual body parts may also be surprisingly achieved by repeated magnetic shielding of that part or of a related anatomical target implicated in the creation of the pain, i.e. a related pain center, as alternative to shielding the entire body within a magnetically shielded room.

The Applicant has demonstrated that pulsed ELF fields of approximately 100 $\mu$T may be generated within a portable, battery-operated device that can effectively provide intensity fields to a specified, location in order to alleviate a variety of disorders. Lower intensity fields may also be effectively utilized with simultaneously shielding of the target tissue from external ambient ELF fields including the Earth's geomagnetic field. This renders portable ELF and pulsed ELF magnetic field therapy devices useful for both diagnosis and treatment of disease.

SUMMARY OF THE INVENTION

The present invention is directed to methods and devices using magnetic shielding and magnetic field stimulation for the treatment (i.e. pain treatment), diagnosis and assessment of disease. The devices of the invention comprise in one embodiment a magnetic field shield. In another embodiment the device comprises a magnetic field generator covered by or embedded within a magnetic field shield. The shield can be targeted to the whole body (i.e. a room can be shielded), or it can be a portable shield device used to target a pain trigger point (e.g. a sleeve covering a limb). It is understood that a magnetic field shield also provides electric field shielding.

In one embodiment, the device of the present invention for providing diagnostic and therapeutic effects comprises a portable magnetic field shield and a weak pulsed magnetic field generator within that shield. This generator may utilize either household current or batteries as sources of electrical power. In a further embodiment of the invention, the device may comprise solely an effective magnetic field shield such as a magnetically shielded room where daily exposures of about 2 hours per day provides pain relief to humans and animals experiencing acute or chronic pain.

Acute exposure (approximately 30 minutes duration) in a shielded room to Cnps of the order of 0.1 $\mu$T in intensity is therapeutic for the treatment of pain, anxiety and depression. The Cnps which are preferred for use in the method and devices of the present invention are as described in Applicant's U.S. Pat. No. 6,234,953 (the entirety of which is incorporated herein by reference). Such Cnps are useful when of 10 to 1000 times smaller magnitude. Such an acute set of Cnps exposures in a shielded room allows for the diagnosis and classification of disease and disability.

According to an aspect of the invention is method for the treatment of physiological disorder in a subject, the method comprising shielding of ambient magnetic fields over the entire body or a portion of the body of a subject for a time effective to reduce and/or alleviate the physiological disorder.

In accordance with another aspect of the present invention is a method for the treatment of acute or chronic pain in a subject, the method comprising repeatedly shielding of ambient magnetic fields over the entire body or a portion of the body of the subject for a time effective to reduce and/or alleviate the acute or chronic pain.

In accordance with another aspect of the present invention is a method for the treatment, diagnosis and/or assessment of diseases in a subject, the method comprising repeatedly shielding of ambient magnetic fields over the entire body or a portion of the body of the subject and simultaneously providing ELF magnetic fields. The subject may be a human or animal.

In accordance with still another aspect of the present invention is a method for the treatment of physiological disorder in a subject, the method comprising simultaneously shielding of ambient magnetic fields over the entire body or a portion of the body of a subject and providing extremely low frequency (ELF) magnetic fields for a time effective to reduce and/or alleviate the physiological disorder.

It is preferred that the intensity of magnetic field stimulation needed for therapeutic and diagnostic procedures is reduced 10- to 1000-fold if the magnetic field stimulation is carried out under ambient magnetic field shielded conditions.

According to a further aspect of the present invention is the use of a portable wearable magnetic shield for treating localized acute or chronic pain in a subject.

According to still a further aspect of the invention is the use of a portable wearable shield simultaneously with magnetic field therapy for treating localized acute or chronic pain in a subject.

According to still a further aspect of the invention is the use of a portable wearable shield simultaneously with magnetic field therapy for treating skeletal abnormalities, such as but not limited to non-union bone fractures or osteoporosis.

According to another aspect of the present invention is a portable magnetic field therapy device, the device comprising a magnetic shield comprising a material with high magnetic susceptibility, wherein said shield is configured to adapt to an anatomical region.

According to another aspect of the present invention is a wearable, portable magnetic field therapy device, the device comprising a magnetic field shield wrap and a magnetic field generating coil. The coil may be battery-operated.

According to another aspect of the present invention is a portable magnetic field therapy device, the device comprising;
  a magnetic shield comprising a material with high magnetic susceptibility, wherein said shield is configured to adapt to an anatomical region
  a magnetic field generating coil associated with said magnetic shield; and
  a power source operably connected to said magnetic field generating coil.

According to another aspect of the present invention is a portable magnetic field therapy device, the device comprising;
  a textile portion which is securable to an anatomical region by way of fasteners; and
  a magnetic shield comprising a material with high magnetic susceptibility, wherein said shield is configured to adapt to an anatomical region, wherein said magnetic shield is secured to said textile portion.

Other aspects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from the detailed description.

BRIEF DESCRIPTION OF THE DRAWINGS

The invention will now be described in relation to the drawings in which.

DETAILED DESCRIPTION OF THE PREFERRED EMBODIMENTS

The applicant has now demonstrated that magnetic field shielding alone or in conjunction with the application of ELF magnetic fields is useful and effective for the treatment of a variety of disorders in humans and animals. Such disorders include but are not limited to acute pain, chronic pain, anxiety, depression, phantom pain, orthopaedic disorders and psychiatric disorders.

Figure 1:
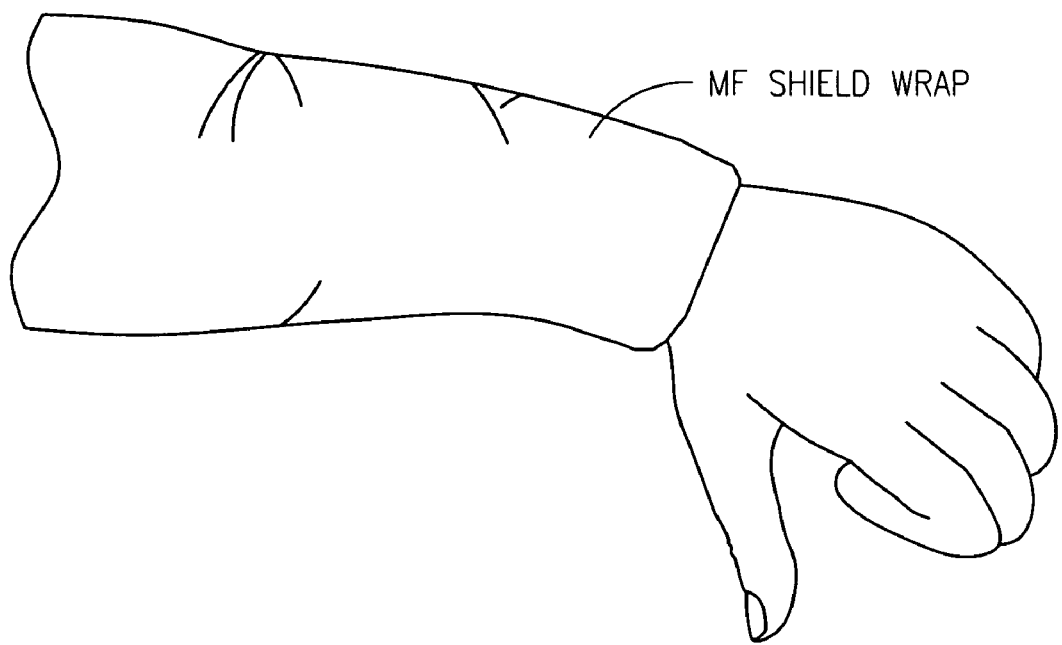
FIG. 1 shows a shielded trigger point and shielded Cnps coil on a human arm.
Figure 2:
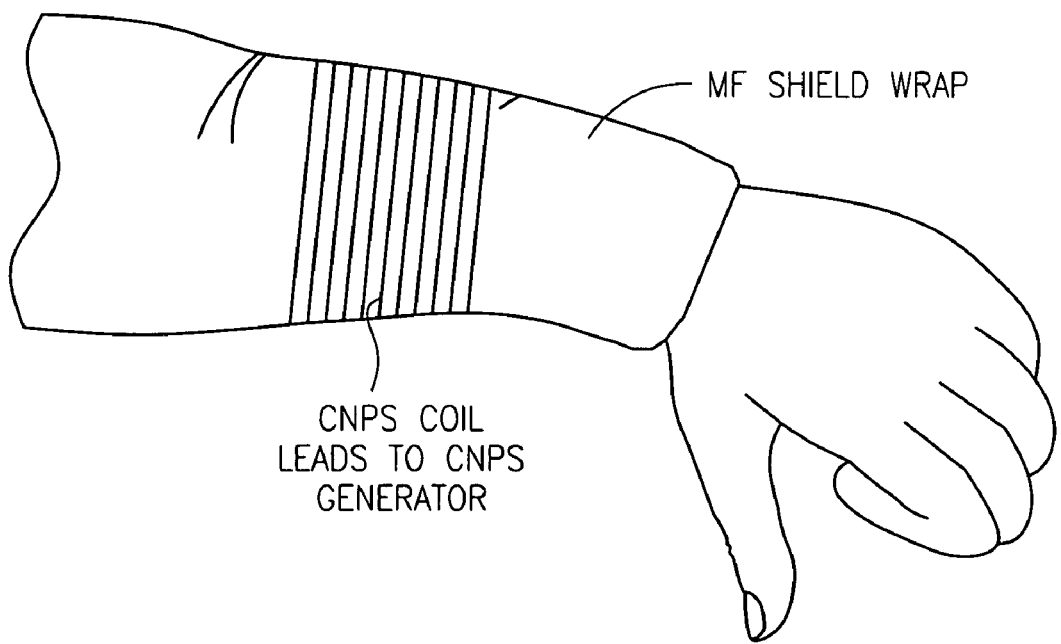
FIG. 2 shows a portable, magnetic field shield designed as a sleeve over a limb, and insulated coils placed under the shield used to produce cnps.
Figure 3:
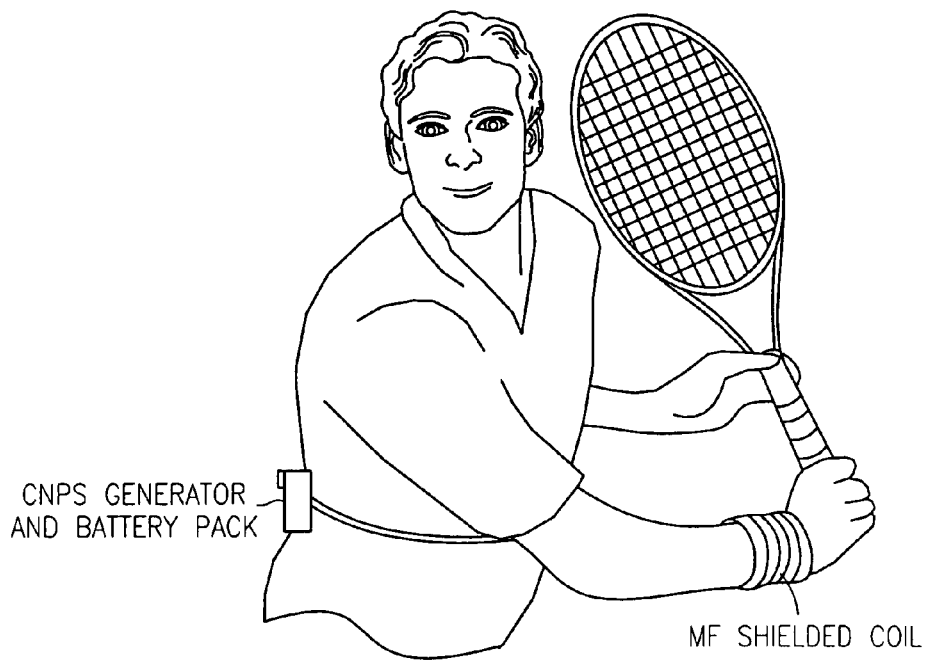
FIG. 3 shows a wearable portable, battery-operated Cnps generator inside a magnetic field shield.

The present invention uses magnetic field shielding either alone or in combination with low intensity magnetic fields to provide treatment, assessment and diagnosis of disease in a subject. This may be accomplished by magnetic shielding to an entire body in a shielded room or a selected body portion by the use of small wearable and portable devices (FIGS. 1, 2 and 3). Subjects suffering from pain for example, may simply wear one or more magnetic shield(s) over the appropriate trigger point(s) for a few hours a day.

Magnetic field shielding can also be used to diagnose a disease state or disorder based on differential physiological effects as a result of magnetic field exposure.

Figure 7:
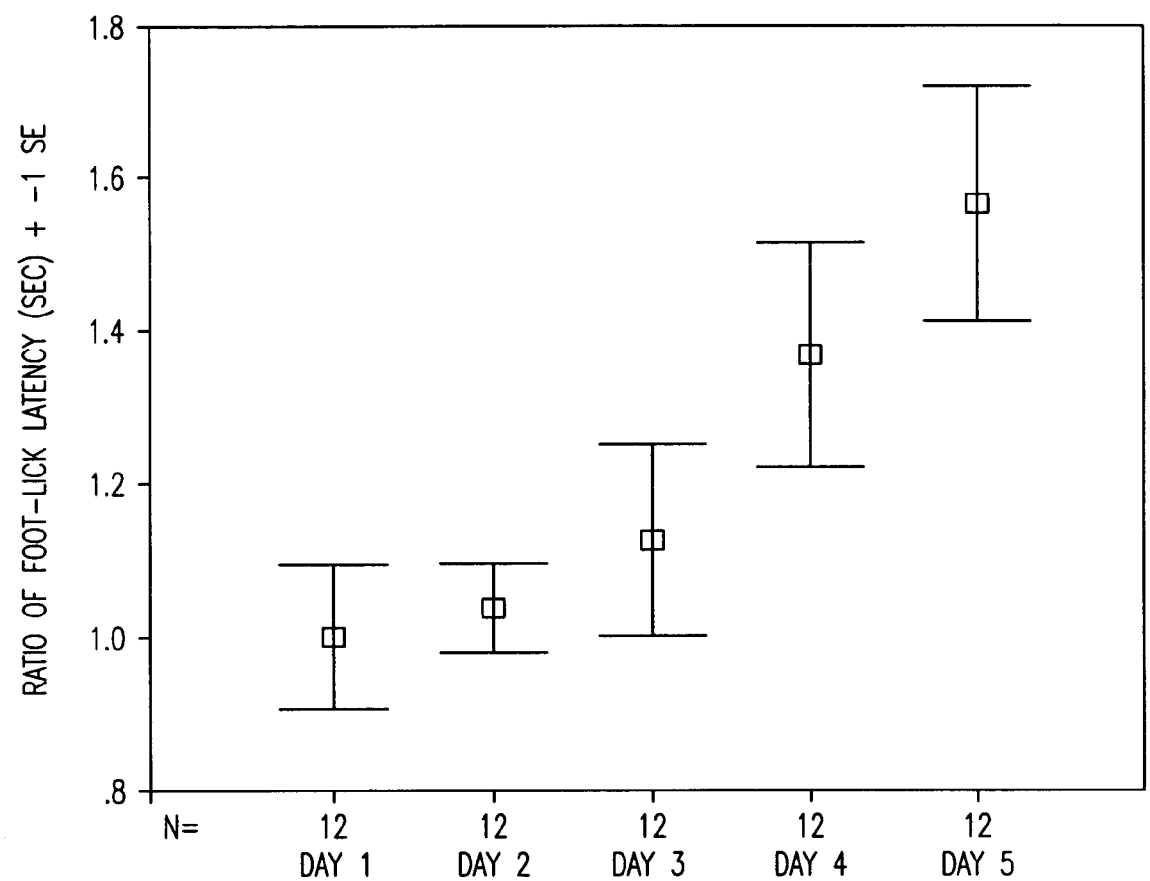
FIG. 7 shows analgesia effects in mice exposed to a magnetic field limiting mu-metal chamber for 60 min. each day for 5 days.

In one embodiment, magnetic shielding in the form of a small wearable and portable Cnps device is particularly useful for the treatment of pain, anxiety and depression. The Cnps magnetic field generator powered by a battery source (FIG. 4) is embedded into or attached onto the inside of a magnetic shield. Using such a device results in rapid pain relief occurring within 30 minutes of the application. In contrast, in another embodiment of the invention, is a shield alone that provides pain relief within hours or days (FIG. 7).

It is therefore advantageous, but not required to use is a shielded Cnps treatment for the first day or two followed by maintenance with the shield alone for the treatment of pain.

Figure 4:
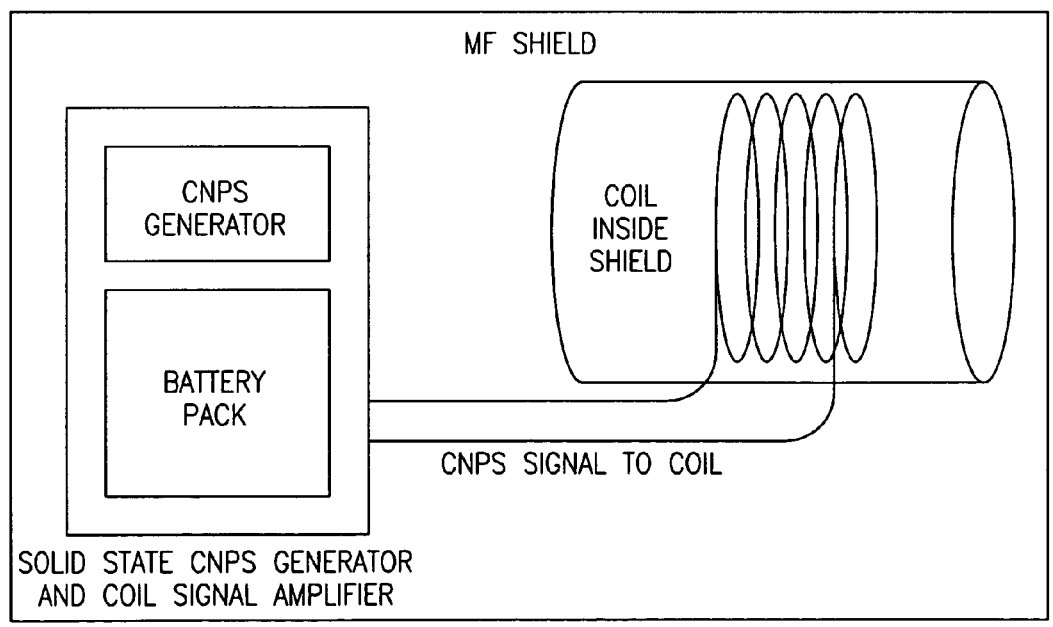
FIG. 4 shows a circuit for a shielded portable Cnps device.

FIG. 4 shows a circuit for a shielded portable Cnps device of the present invention. One battery powers a microchip programmed with the relevant Cnps pulse while the second battery provides power to the miniature amplifier which is then connected to the transformer wire embedded into insulator located on the inside of the magnetic shield. One skilled in the art would understand that a variety of modifications can be made to such device and circuit so long as a suitable magnetic field be generated.

Figure 5:
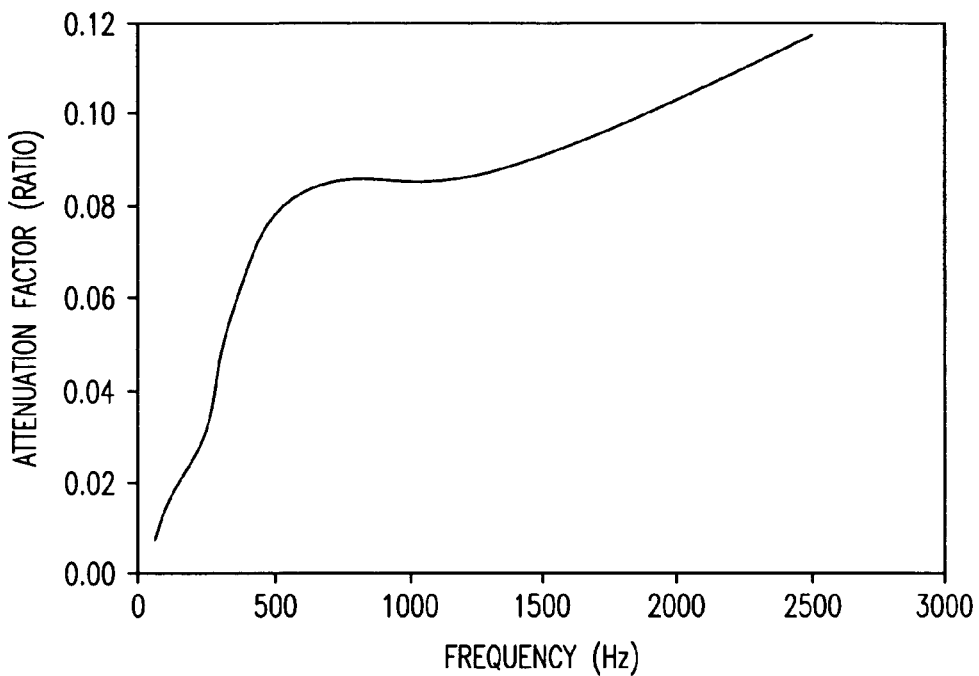
FIG. 5 shows the attenuation of magnetic fields as a function of frequency for a typical mu-metal box.

Magnetic field shielding is designed for attenuation of ELF frequencies from zero (shielding to the static Earth's geomagnetic field) to 2 kHz by an approximate factor of 10 or more (FIG. 5). Materials with high magnetic susceptibility are preferred for use as a magnetic shield device in the present invention which could include but are not limited to metals such as iron or nickel and proprietary metals like mu-metal and combinations thereof.

Magnetic shielding for therapy and diagnosis can be used in two different ways: a) with only the shield, and b) with a Cnps magnetic field generator which produces an ELF magnetic field in a target tissue which is shielded from ambient magnetic fields other than those produced by the Cnps generator.

Magnetic Field Shield Alone

Two forms of treatment are possible with the magnetic shield alone: a) one in which the entire body is treated in a shielded room, and the other b) in which only part of the body is treated using a "wearable" magnetic shield.

ELF Magnetic field shielding increases as one moves towards the center of the device away from its open ends. The shield must be designed such that the tissue to be treated is shielded by at least a factor of 10. This may result in different designs incorporating different shielding metals at different distances from the open ends of the magnetic shield. It is understood by one of skill in the art that the device can be of several different types of designs. For example, in one design, the sleeve is a permanent thin cylinder while in the other design, it can open and close through the use of soft shielding metal and end overlap secured by a fastener such as Velcro™ strips. Another design can be configured for tight fitting around anatomical joints such as a wrist or an ankle. Still yet in another design, one end of the cylinder is capped for placement over the end of a body part such as the foot, hand or head.

Whole-Body Treatment

For the whole-body treatment, the subject is put into a shielded room for a minimum of approximately 1 hour a day everyday. This provides relief from widespread chronic pain. Subjects with acute pain of only a few days of anticipated duration should not be so treated as the exposure for the first two or three days will not provide significant relief (FIG. 7). In fact, for subjects with chronic pain, it is preferred that the first few days of treatment be combined with other physical (Cnps) or pharmacological pain treatments. For severe chronic pain, subjects may increase their number of sessions from 1 per day to 2 or 3 equally spaced periods per day and/or exposure durations increased.

Partial-Body Treatment

For the treatment of pain in part of the body that can be treated locally, i.e. with a local anaesthetic, a wearable shield is more convenient, economical and desirable than whole-body treatment. For pain anticipated to be endured more than a week, subjects may attach a portable/wearable shield (FIGS. 1, 2) for one to three 1-2-hour periods a day. This can be continued with other physical (e.g. Cups) or pharmaceutical treatments for pain relief.

Magnetic Field Shield Combined with a Cnps Generator

Two forms of treatment are encompassed by the present invention: a) one in which the entire body or portions of the body are exposed to Cnps magnetic fields while the entire body is magnetically shielded from external non-Cnps fields, and b) one in which only part of the body is treated using a "wearable" device comprised of a magnetic shield and Cnps generator (FIG. 4, 5).

Whole-Body/Large Portions of Body Treatment

In a magnetically shielded room, the subject's whole body or large portions of the subject's body are treated with Cnps pulses. These treatments may be for any condition for which Cnps or other magnetic fields are effective, including diagnostic use. The field strengths used will be 10 to 1000 times lower than those needed in an unshielded room. The subjects can be treated for either acute or chronic conditions with or without other medications including physical (electro-convulsive shock) or pharmaceutical. Treatments can be 1 to 10 times per day as treatment periods will usually be less than 30 minutes each for therapeutic use and diagnostic use may require as little as only one session.

Partial Body Treatment

For the treatment of the brain in psychiatric disorders or for diagnostic testing when only part of the body is to be exposed to Cnps, wearable devices as shown in FIGS. 2 and 3 are much more convenient, not requiring a magnetically shielded room. For the ambulatory subject, a battery-operated device is best. For the treatment of acute pain lasting less than a week, the subject can wear the device continually and the Cnps fields can be cycled on for 30 minutes every 2 hours. For subjects in chronic pain, treatment for the first week would be same as for the subject in acute pain but after the first week, Cnps fields would be generated less and the device removed for all but for about three 2 hr periods per day. For other acute treatments such as depression, the Cnps may be applied approximately daily for 30 min periods with an extremity-designed device (FIG. 2).

It is important for the generator to produce a fairly uniform field near the center of the shield. Therefore, Helmholz or Merritt volume coil designs are preferred. These coils are embedded into an electrical insulator located between the magnetic shield and the inside surface of the device. As with the shield shown in FIG. 2, there is the same need for permanent cylindrical designs and those that can open. Electrical connectors will be needed at the openings for the volume coils to maintain electrical integrity.

It is understood by one of skill in the art that the magnetic shield device either alone or having a magnetic field generator incorporated therein may be provided secured by various means to a textile type of "bandage" that is durable and stretchable and can be tightly affixed to a particular anatomical region and held together by fasteners.

It is further understood by one of skill in the art that the Cnp can be delivered by surface coils rather than volume coils especially if the target is a small region such as a pain trigger point. When such surface coils are used electrical conductors may not be needed at the openings of partial body magnetic shields.

Lastly, it is also understood that one of skill in the art could readily use magnetic shielding and magnetic fields (Cnps) to devise effective treatment regimes for a variety of disorders in a subject based on the present teachings. All such treatment and usage regimes are encompassed within the scope of the present invention. As such a variety of portable magnetic shield devices alone or in combination with a Cnps generator may be developed in addition to that specifically described herein and still fall within the scope of the presently described and claimed invention.

EXAMPLES

The examples are described for the purposes of illustration and are not intended to limit the scope of the invention.

Methods involves in magnetic field generation referred to but not explicitly described in this disclosure and examples are reported in the scientific literature and are well known to those skilled in the art.

Example 1

Analgesic Effects of Magnetic Field Shielding in Mice

Figure 6:
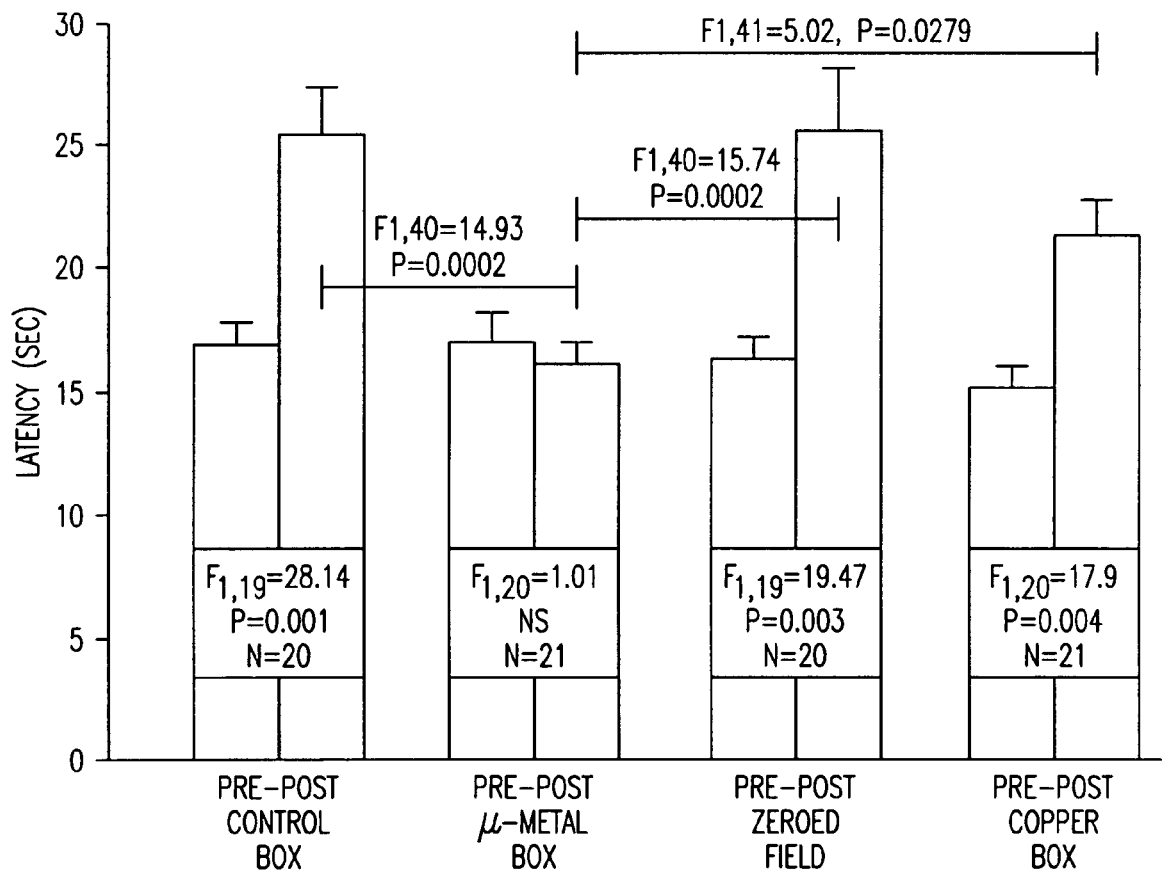
FIG. 6 shows nociceptive response of CD-1 mice exposed to a Control condition box, a mu-metal box, a Copper box, or a 3-D zeroed MF condition.

The effects of a 90 min. exposure of mice to the reduced ambient magnetic fields while enclosed in a mu-metal box was demonstrated (FIG. 6). FIG. 5 shows the amount the magnetic fields are shielded by the mu-metal box. Following the 90 min. exposure, analgesia was induced in the mice and then the mice were tested 30 min. later for increased analgesia and compared to analgesic levels prior to entry into the mu-metal box. Note that the single 90 min. in the mu-metal box reduced the analgesic levels but 90 min. in a control box which does not shield for electric or magnetic fields, had no effect and 90 min. in a copper box, which screens for electric fields, also had no effect Similarly just zeroing the static component of the ambient magnetic field and exposing mice to the zeroed static field had no effect. This indicates that 1) when in a low magnetic field environment mouse behaviour is altered by the absence of weak extremely low frequency magnetic fields (<0.1 µT) and 2) the first exposures shielded ambient magnetic fields may increase sensitivity to pain if the patient is on an analgesic and 3) in a magnetically shielded environment exposures to fields as weak as 0.1 µT can alter analgesic behaviour.

Repeated exposures to shielded ambient magnetic fields will was demonstrated to induce analgesia in mice (FIG. 7). CD-1 mice were pre-tested on a hotplate (50° C.) for latency to a foot-lick (recorded in sec.). Increase of latency over pre-tested values indicates an analgesic effect. After pre-test mice were placed within a magnetic field limiting mu-metal chamber for 60 min. and then re-tested on a hotplate for foot-lick latency each day for 5 days. The ratio of foot-lick latency is used to normalize for individual differences and is the re-test time divided by the pretest time. A ratio greater than 1 represents the induction of nociception (analgesia). The induction of analgesia is significant [$F1,11=6.76$, $P=0.025$, $Eta^2=0.38$] when examining pre-test vs re-test and also increases significantly from day 1 through day 5 [$F4, 8=8.31$, $P=0.006$, $Eta^2=0.63$]. Hence patients exposed just to magnetic field shielding for 1 hour per day will begin experiencing pain relief by the third or fourth day.

Example 2

Magnetic Shielding Treatment—Cancer Subjects—Chronic Pain

A subject with terminal cancer and in chronic pain schedules receives treatment in a magnetically shielded room for a morning period of 1 to 2 hours and a period of an additional 2 hours around the dinner hour. This allows the subject to reduce morphine use and, being more alert during these periods, is in a better state to enjoy meals and visits during breakfast and dinner. For the first week only, the subject is exposed to a Cnps generator while in the shielded room.

Psychiatric Subject in a Drug-Resistant Depression

The subject receives a 30-minute treatment once a day in the morning with a shielded Cnps exposure system. The system is placed over the head. The subject no longer requires anti-depressants with their annoying side-effects or electroconvulsive shock therapy with the required anaesthetic and does not have fears of memory loss from the procedure.

Acute Treatment of Arthritis Pain

A middle-aged man may prepare for an afternoon game of golf by strapping on two shielded Cnps devices, one over a painful wrist and the other over an arthritic ankle. Switching on the two devices enroute between home and golf course, provides relief in both sites. During the game, the wrist unit may be removed and the ankle unit turned off. Between the first and second 9 holes, treatment may be resumed.

Chronic Treatment of Arthritis Pain

A middle-aged woman suffering from chronic rheumatoid arthritis pain in both wrists may wear a shielded Cnps unit during the day, having it programmed to turn on and off once every 2 hours during the day. At night, the unit may be removed and pain medication may be taken prior to bed. The pharmaceutical pain medication is more effective because physiological tolerance is delayed as the same medication (or a reduced dose) does not have to be taken during the day.

Chronic Treatment of Phantom Limb Pain

An amputee suffering from debilitating phantom limb pain from the removal of one arm below the elbow may wear a shielded Cnps device continually. The device has three programmed modes. During the day, it switches on for 30 minutes every 2 hours, generating a Cnps pulse in the target tissue. During the evening, the magnetic shield itself provides pain relief provided geomagnetic-like fields are intermittently generated by the coils inside the shield. This exposure pattern is controlled by a programmed microprocessor which is part of the Cnps generator (FIG. 3).

Treatment with other ELF Magnetic Fields

A subject suffering from a non-union fracture has a shield and an ELF magnetic field generator built into a limb cast. The subject's non-union fracture is exposed for 3 hours per day to pulsed ELF magnetic fields shown to stimulate union, during which time, the subject can be ambulatory. In the past, the subject would have had to report to a clinic to be exposed, but due to the shielding, much lower intensity fields can be used and these can be provided by a battery. Subjects suffering from other orthopaedic diseases such as osteoporosis can also be treated in the home a few hours a day using similar wearable devices.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

BIBLIOGRAPHY

Betancur C., Dell'Olmo G., Alleva E. Magnetic field effects on stress-induced analgesia in mice: Modulation by light. *Neurosci Lett* 1994, v182, p147-150.

Choleris E., Del Seppia C., Thomas A.W., Luschi P, Ghione S, Papi F, Prato FS. Shielding but not zeroing of the ambient magnetic field reduces stress-induced analgesia in mice; submitted to *Proc R Soc Lond B*, June 2001.

Del Seppia C., Luschi P., Ghione S., Crosio E., Choleris E., Papi F. Exposure to a hypogeomagnetic field or to oscillating magnetic fields similarly reduce stress-induced annualise in C57 mice. *Life Sciences*, 2000, v66, p1299-1306.

Deutschlander M.E., Phillips J.B., Borland S.C. The case for light-dependent magnetic orientation in animals. *J Exp Biol* 1999, v202, p891-908.

Kavaliers M., Ossenkopp K.P. Tolerance to morphine-induced analgesia in mice: magnetic fields function as environmental specific cues and reduce tolerance development. *Life Sciences* 1985, v37, 1125-1135.

Kavaliers M., Ossenkopp K.P. Repeated naloxone treatments and exposures to weak 60 Hz magnetic fields have "analgesic" effects in snails. *Brain Research* 1993, v620, p159-162.

Lednev V.V., Srebnitskaya L.K., Ye N., Il'yasova Z., Rozhdestvenskaya Y., Klimov A.A, Belova N.A., Tiras K.P. Magnetic parametric resonance in biosystems: Experimental verification of the predictions of a theory using regenerating planarians, *Dugesia tigrina*, as a test system. *Biophysics* 1997, v41, p825-835.

McLeod K.J., Lee RC, Ehrlich H.P. Frequency dependence of electric field modulation of fibroblast synthesis. *Science* 1987, v236, p1465-1469.

Papi F., Ghione S., Rosa C., Del Seppia C., Luschi P. Exposure to oscillating magnetic fields influences sensitivity to electrical stimuli: II: Experiments in humans. *Bioelectromanetics* 1995, v16, p295-300.

Thomas A.W., Kavaliers M., Prato F.S., Ossenkopp K.P. Analgesic effects of a specific pulsed magnetic field in the land snail, *Cepaea nemoralis*: Consequences of repeated exposures, relations to tolerance and cross-tolerance with DPDPE. *Peptides* 1998, v19, #2, p333-342.

Thomas A.W., White K.P., and Prato F.S. Rheumatoid arthritis and fibromyalgia subjects exposed to a specific pulsed 200 µT Magnetic Field: effects on normal standing balance. *Bioelectromagnetics Soc Abstracts* 2000 v21.

All publications, patents, and patent applications are incorporated by reference herein, as though individually incorporated by reference.

The invention claimed is:

1. A method for treating a physiological disorder in a subject comprising providing a source of extremely low frequency (ELF) pulsed magnetic fields (Cnps), applying the extremely low frequency (ELF) pulsed magnetic fields (Cnps) to at least a portion of a body of the subject and entirely shielding the source and the portion from low frequency ambient magnetic fields for a time effective to reduce or alleviate the physiological disorder.

2. The method of claim 1, wherein said physiological disorder is pain, anxiety, depression, phantom pain or orthopedic disorders.

3. The method of claim 2, wherein said orthopedic disorder is non-union fractures or osteoporosis.

4. The method of claim 2, wherein said shielding is provided for 0.5 to 3 hours per day.

5. The method of claim 4, wherein said shielding is provided 2 to 3 times a day.

6. The method of claim 4, wherein said shielding is provided for 1 to 2 hours per day.

7. The method of claim 2, wherein said shielding is provided to a selected body portion.

8. A portable magnetic field therapy device comprising a magnetic shield configured to adapt to an anatomical region, with an inner side oriented towards the anatomical region, comprising a material with high magnetic susceptibility and a portable magnetic field generator that produces an extremely low frequency (ELF) pulsed magnetic field, the magnetic field generator being entirely on the inner side of the magnetic shield, wherein the device is a cylinder and said cylinder is slit along the length and wherein fasteners are provided to secure said slits together.

9. The device of claim 8, wherein said material is a metal providing magnetic field shielding.

10. The device of claim 8, wherein said material is iron.

11. The device of claim 8, wherein said material is a metal alloy comprising mu-metal.

12. A portable magnetic field therapy device comprising:
a magnetic shield configured to adapt to an anatomical region comprising a material with high magnetic susceptibility, the magnetic shield having an inner side oriented towards the anatomical region;
a magnetic field generating coil entirely positioned on the inner side of the magnetic shield;
a power source operably connected to said magnetic field generating coil; and
a textile portion adapted to secure the device to the anatomical region.

* * * * *